(12) United States Patent
Betageri (10) Patent No.: US 8,889,180 B2
(45) Date of Patent: *Nov. 18, 2014

(54) COATED DRUG DELIVERY FORMULATIONS

(75) Inventor: Guru V. Betageri, Chino Hills, CA (US)

(73) Assignee: Western University of Health Sciences, Pomona, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 13/269,281

(22) Filed: Oct. 7, 2011

(65) Prior Publication Data

US 2012/0027864 A1 Feb. 2, 2012

Related U.S. Application Data (63) Continuation of application No. 10/999,831, filed on Nov. 30, 2004, now Pat. No. 8,658,202, and a continuation-in-part of application No. 10/132,665, filed on Apr. 24, 2002, now Pat. No. 6,849,269, which is a continuation-in-part of application No. 09/931,399, filed on Aug. 16, 2001, now Pat. No. 6,759,058.

(60) Provisional application No. 60/286,386, filed on Apr. 25, 2001.

(51) Int. Cl.
A61K 9/127 (2006.01)
A61K 9/14 (2006.01)
A61K 31/426 (2006.01)
A61K 31/568 (2006.01)
A61K 31/64 (2006.01)
A61K 9/50 (2006.01)

(52) U.S. Cl.
CPC ............. *A61K 31/426* (2013.01); *A61K 9/1277* (2013.01); *A61K 31/568* (2013.01); *A61K 31/64* (2013.01); *A61K 9/5047* (2013.01)
USPC ............ 424/450; 424/451; 424/489; 424/463

(58) Field of Classification Search
CPC ........ A61K 9/127; A61K 9/14; A61K 9/4891
USPC .................................. 424/450, 489, 451, 463
See application file for complete search history.

(56) References Cited

U.S. PATENT DOCUMENTS

| | | | |
|---|---|---|---|
| 4,508,703 A | 4/1985 | Redziniak et al. | |
| 4,615,885 A | 10/1986 | Nakagame et al. | |

(Continued)

FOREIGN PATENT DOCUMENTS

| | | |
|---|---|---|
| CN | 1274605 A | 11/2000 |
| DE | 4038075 C1 | 3/1992 |

(Continued)

OTHER PUBLICATIONS

Ahn, Byung-nak et al. "Preparation and evaluation of proliposomes containing propranolol hydrochloride", J. Microencapsulation, 1995, No. 4, pp. 363-375.

(Continued)

*Primary Examiner* — Gollamudi Kishore
(74) *Attorney, Agent, or Firm* — J.A. Lindeman & Co., PLLC (57) ABSTRACT

The invention relates generally to methods of making formulations for delivering biological agents to a patient. In one aspect, proliposomal drug-delivery systems for medicaments are provided. In another aspect, coated proliposomal formulations for poorly water soluble drugs, and methods for making the same, are provided. Certain embodiments of the present invention provide enhanced stability and bioavailability for pharmaceutical formulations.

20 Claims, 2 Drawing Sheets

(56) References Cited

U.S. PATENT DOCUMENTS

| | | | |
|---|---|---|---|
| 4,744,989 A | | 5/1988 | Payne et al. |
| 4,849,227 A | | 7/1989 | Cho |
| 4,920,016 A | | 4/1990 | Allen et al. |
| 5,019,591 A | | 5/1991 | Gardner et al. |
| 5,049,388 A | * | 9/1991 | Knight et al. ............... 424/450 |
| 5,206,219 A | * | 4/1993 | Desai ......................... 424/85.2 |
| 5,505,967 A | | 4/1996 | Geary et al. |
| 5,635,206 A | * | 6/1997 | Ganter et al. ............... 424/450 |
| 5,643,599 A | | 7/1997 | Lee et al. |
| 5,665,700 A | | 9/1997 | Cho et al. |
| 5,709,879 A | | 1/1998 | Barchfield et al. |
| 5,811,119 A | * | 9/1998 | Mehta et al. ............... 424/450 |
| 5,888,550 A | | 3/1999 | Cook et al. |
| 5,922,324 A | | 7/1999 | Aga et al. |
| 5,972,389 A | | 10/1999 | Shell et al. |
| 6,015,576 A | * | 1/2000 | See et al. ..................... 424/450 |
| 6,133,026 A | | 10/2000 | Huang et al. |
| 6,156,731 A | | 12/2000 | Grass |
| 6,180,604 B1 | | 1/2001 | Fraser et al. |
| 6,187,335 B1 | | 2/2001 | Brey et al. |
| 6,218,016 B1 | | 4/2001 | Tedeschi et al. |
| 6,224,910 B1 | | 5/2001 | Ullah et al. |
| 6,309,663 B1 | | 10/2001 | Patel et al. |
| 6,432,928 B1 | * | 8/2002 | Szente et al. ................. 514/58 |
| 6,511,676 B1 | | 1/2003 | Boulikas |
| 6,759,058 B1 | * | 7/2004 | Betageri ...................... 424/450 |
| 6,761,901 B1 | | 7/2004 | Betageri et al. |
| 6,849,269 B2 | * | 2/2005 | Betageri ...................... 424/450 |
| 6,956,021 B1 | | 10/2005 | Edwards et al. |
| 7,387,791 B2 | * | 6/2008 | Betageri et al. ............. 424/450 |
| 2001/0008638 A1 | * | 7/2001 | Wilding ....................... 424/468 |
| 2001/0024658 A1 | | 9/2001 | Chen et al. |
| 2001/0055610 A1 | | 12/2001 | Nagata et al. |
| 2002/0187189 A1 | | 12/2002 | Betageri |
| 2003/0078194 A1 | | 4/2003 | Cho et al. |
| 2003/0170298 A1 | | 9/2003 | Garces et al. |

FOREIGN PATENT DOCUMENTS

| | | |
|---|---|---|
| DE | 19825856 A1 | 12/1999 |
| EP | 00 87993 | 9/1983 |
| EP | 0087993 A | 9/1983 |
| EP | 0648487 A | 4/1995 |
| EP | 1138312 | 10/2001 |
| EP | 1138312 A | 10/2001 |
| FR | 2581543 | 11/1986 |
| JP | H01500589 A | 3/1989 |
| JP | 07109219 | 4/1995 |
| JP | 07109219 A | 4/1995 |
| JP | 2002523360 A | 7/2002 |
| JP | 2003528894 A | 9/2003 |
| JP | 2003534252 A | 11/2003 |
| JP | 2004535838 A | 12/2004 |
| WO | 9428876 | 12/1994 |
| WO | WO 94/28876 | 12/1994 |
| WO | 0010541 | 3/2000 |
| WO | 0182897 | 11/2001 |
| WO | WO 01 82897 | 11/2001 |
| WO | 0213782 A1 | 2/2002 |
| WO | WO2005/020708 | 3/2005 |
| WO | WO2005/070401 | 8/2005 |
| WO | WO2006/060325 | 6/2006 |
| WO | WO2007/054342 | 5/2007 |
| WO | WO2008/106772 | 9/2008 |

OTHER PUBLICATIONS

Chen et al. "Lectin-bearing Polymerized Liposomes as Potential Oral Vaccine Carriers", Pharmaceutical Research, vol. 13, No. 9, 1996, pp. 1378-1383.

Deo, MR et al. "Proliposome-based transdermal delivery of levonorgestrel", J. Biomater Appl., Jul. 1997; 12(1): 77-88. Abstract in one page.

Dufour, P et al. "Characterization of enzyme immobilization in lipsomes prepared from proliposomes", J. Microencapsulation, 1996, vol. 13, No. 2, pp. 185-194.

Katare, OP et al. "Effervescent granule based proliposomes of ibuprofen", J. Microencapsul, Oct.-Dec. 1990; 7(4): 455-62. Abstract in one page.

Katare, OP et al. "Enhanced in vivo performances of liposomal indomethacin derived from effervescent granule based proliposomes", J. Microencapsulation, 1995, vol. 12, No. 5, pp. 487-493.

Payne, NI et al. Proliposomes: A Novel Solution to an Old Problem, Journal of Pharmaceutical Sciences, Apr. 1986, vol. 75, No. 4, pp. 325-329.

Payne, NI et al. "Characterization of Proliposomes", Journal of Pharmaceutical Sciences, 1986, 75(4): 330-332.

Perrett, S et al. "A simple method for the preparation of liposomes for pharmaceutical applications: characterization of the liposomes", J. Pharm Pharmacol, Mar. 1991; 43(3): 154-161. Abstract in one page.

Betageri, GV. Poster Presentation at the American Association of Pharmaceutical Scientists Meeting in Indianapolis in Nov. 2000.

International Search Report of Dec. 18, 2002 in application WO2002085304.

International Search Report of Jun. 20, 2006 in application WO2006060325.

Montenegro L, et al., "Quantitative determination of hydrophobic compound entrapment in dipalmitoylphosphatidylcholine liposomes by differential scanning calorimetry," Int. J. of Pharmaceutics, vol. 138, No. 2, pp. 191-197, Jul. 26, 1996.

European Search Report and Opinion of Jan. 23, 2013 in EP 12001745.4, dated Jan. 23, 2013.

Supplementary European Search Report of Jan. 12, 2010 in application No. EP 05 85 2301.

Bodmeier, "Tableting of coated pellets," 43 European Journal of Pharmaceutics and Biopharmaceutics 1 (1997).

Chung, SJ, Future drug delivery research in South Korea, J. Control Release, Nov. 1, 1999; 62(1-2): 73-79. Abstract in two pages.

Deo, MR, Sant, VP, Parekh, SR, Khopade, AJ, Banakar UV, "Proliposome-based transdermal delivery of levonorgestrel", J. Biomater Appl., Jul. 1997; 12(1): 77-88. Abstract in one page.

Perrett, S, Golding, M, Williams, WP, "A simple method for the preparation of liposomes for pharmaceutical applications: characterization of the liposomes", J. Pharm Pharmacol, Mar. 1991; 43(3): 154-161. Abstract in one page.

Katare, OP, Vyas, SP, Dixit, VK, "Effervescent granule based proliposomes of ibuprofen", J. Microencapsul, Oct.-Dec. 1990; 7(4): 455-62. Abstract in one page.

Chen, Hongming, Torchillin, Vladimir and Langer, Robert, "Lectin-bearing Polymerized Liposomes as Potential Oral Vaccine Carriers", Pharmaceutical Research, vol. 13, No. 9, 1996, pp. 1378-1383.

Dufour, P, Vuillemard, JC, Laloy, E, and Simard, RD, "Characterization of enzyme immobilization in lipsomes prepared from proliposomes", J. Microencapsulation, 1996, vol. 13, No. 2, pp. 185-194.

Ahn, Byung-nak, Kim, Shin-Keun, and Shim, Chang-Koo, "Preparation and evaluation of proliposomes containing propranolol hydrochloride", J. Microencapsulation, 1995, No. 4, pp. 363-375.

Katare, OP, Vyas, SP, and Dixit, VK, "Enchanced in vivo performances of liposomal indomethacin derived from effervescent granule based proliposomes", J. Microencapsulation, 1995, vol. 12, No. 5, pp. 487-493.

Payne, Nicholas I, Timmins, Peter, Ambrose, Cheryl V, Ward, Michael D, and Ridgway, Frank, Proliposomes: A Novel Solution to an Old Problem, Journal of Pharmaceutical Sciences, Apr. 1986, vol. 75, No. 4, pp. 325-329.

Payne, Nicholas I, Browning, Ivan, and Hynes, Cheryl A, "Characterization of Proliposomes", Journal of Pharmaceutical Sciences, 1986, 75(4): 330-332.

Poster presented by Dr. Guru V. Betageri at the American Association of Pharmaceutical Scientists Meeting in Indianapolis in Nov. 2000.

Supplementary European Search Report Issued in Related European Application No. EP 02 72 5809, Completed Aug. 26, 2009, and Mailed Sep. 2, 2009.

(56) References Cited

OTHER PUBLICATIONS

Kumar et al., "Formulation, Characterization, and In Vitro Release of Glyburide from Proliposomal Beads," Drug Delivery: Journal of Delivery and Targeting of Therapeutic Agents, 2001, pp. 25-27, vol. 8, No. 1.

Takeuchi, et al., "Mucoadhesive Liposomes Coated with Chitosan or Caropol for Oral Administration of Peptide Drugs," Proceedings of the International Symposium on Controlled Release Bioactive Materials, 1999, pp. 988-989, vol. 26.

Abstract of FR 2581543, Nov. 1986.

* cited by examiner

COATED DRUG DELIVERY FORMULATIONS

RELATED APPLICATIONS

This application is a continuation-in-part of co-pending U.S. application Ser. No. 10/132,665, filed Apr. 24, 2002, which is a continuation-in-part of U.S. application Ser. No. 09/931,399, filed Aug. 16, 2001, now U.S. Pat. No. 6,759,058, which claims benefit to U.S. Provisional Application No. 60/286,386, filed Apr. 25, 2001, the entire teachings of which are incorporated herein by reference.

BACKGROUND OF THE INVENTION

1. Field of the Invention

This invention relates generally to delivery systems for formulations comprising biologically active agents. In one embodiment, the invention relates to coated proliposomal formulations for poorly water soluble drugs.

2. Description of the Related Art

Pharmaceutical formulations may be administered through various routes of administration. For example, drugs may be administered orally, intravenously, subcutaneously and by aerosol. The encapsulation of pharmaceuticals in liposomes is useful in reducing toxicity and improving the therapeutic effectiveness of certain drugs. For example, compounds such as insulin, factor VIII, tryptophan, phenylalanine, heparin, vitamin K etc., have been investigated for their effectiveness orally, after encapsulation into liposomes. Although they represent an improvement over the prior art, oral liposome formulations have been criticized because of their instability, leakage and potential destruction in gastric fluids.

The use of proliposomes represents an alternative to conventional liposomal formulations. Proliposomes are dry, free-flowing granular products, which, upon the addition of water, disperse to form a multilamellar liposomal suspension. The stability problems associated with conventional liposomes, including aggregation, susceptibility to hydrolysis and oxidation, may be avoided by using proliposomes. The use of proliposomes is well-known in the pharmaceutical field.

Among the various routes of drug administration, the oral route is advantageous for some drugs in certain instances because of its versatility, safety and patient comfort. Although the oral ingestion of drugs represents a safe and versatile method of pharmaceutical delivery, the therapeutic efficacy of many drugs may be reduced because many pharmaceuticals are labile or inactivated under the acidic conditions of the stomach. Enteric coating materials have been applied to address this deficiency. Non-enteric coating also offer several advantages for both oral and non-oral routes of administration. Accordingly, the present invention, in some embodiments, provides novel formulations, coated with enteric or non-enteric coatings, and methods of making those formulations.

SUMMARY OF THE INVENTION

Although the use of proliposomes and the use of enteric and non-enteric coatings are independently known in the art, the combination of a coating with a proliposomal formulation has not been disclosed. Surprisingly, when a coating of some embodiments of the current invention is combined with a proliposomal formulation of some embodiments of the current invention, drug delivery is enhanced. In many embodiments of the present invention, this novel and unexpected enhancement, which results from the unique combination of a coating and a proliposomal formulation, relates to increased drug absorption, stability and bioavailability.

In many embodiments of the current invention, the combination of a coating and a proliposomal formulation overcomes the disadvantages of drug delivery systems known in the prior art. For example, the utility of previous systems for orally administering labile pharmacological substances has been limited by the need to use toxic amounts of delivery agents, the instability of the systems, the inability to protect the active ingredient, the inability to effectively deliver drugs that are poorly water soluble or labile, the inadequate shelf life of the systems, the failure of the drug delivery systems to promote absorption of the active agent and the difficulties inherent to manufacturing the systems. Several embodiments of the present invention overcome one or more of these disadvantages.

In some embodiments, a formulation comprising a biologically active agent is produced by application of one or more enteric coatings. In other embodiments, a formulation comprising a biologically active agent is produced by application of one or more non-enteric coatings.

The term "enteric coating," as used herein, shall be given its ordinary meaning and shall also include materials that permit acid-labile drugs to remain active in the stomach upon oral ingestion such that the active ingredient is released and absorbed in the intestine. Enteric coatings materials are well known in the pharmaceutical art and include alginates, alkali-soluble acrylic resins, hydroxypropyl methylcellulose phthalate, cellulose acetate phthalate, and the like. Enteric coatings may be used for oral routes of administration. Enteric coatings may be used for non-oral routes of administration. For example, enteric coatings may be useful for transdermal applications, as well as for other non-oral routes.

The term "acid-labile," as used herein, shall be given its ordinary meaning and shall also include drugs, compositions, or materials (e.g., coating materials) that degrade in acidic environments, dissolve in acidic environments, are unstable in acidic environments, and/or are inactivated in acidic environments.

The term "non-enteric coating," as used herein, shall be given its ordinary meaning, and as such, includes acid-labile materials and/or materials that degrade in the stomach, or other acidic environments. Non-enteric coatings are useful for both oral and non-oral routes of administration.

Several embodiments of the current invention are particularly advantageous because they offer a simple and inexpensive system to facilitate the administration of medicaments and other agents. In many embodiments, a drug delivery system according to some embodiments of the invention enhances the stability and bioavailability of biologically active agents.

In one embodiment of the invention, a method of making a formulation suitable for administration to a patient is provided. In one embodiment, this method comprises providing one or more phospholipids, providing one or more biologically active agents, exposing simultaneously at least a portion of the biologically active agents and at least a portion of the phospholipids to a non-aqueous solvent, removing the non-aqueous solvent, thereby making a powder. The powder comprises one or more phospholipids and one or more biologically active agents. The method, in some embodiments, further comprises coating the powder with one or more acid-labile coatings, thereby making coated particles. The acid-labile coatings contacts at least a portion of the powder.

In one embodiment, the acid-labile coating is a material selected from the group consisting of one or more of the following: a cellulose-based agent, povidone, and polyethylene. In one embodiment, the cellulose-based agent is selected from the group consisting of one or more of the following: methylcellulose, ethylcellulose, hydroxyethylcellulose, methylhydroxyethylcellulose, hydroxypropylcellulose, hydroxypropylmethylcellolose, and sodium carboxymethylcellulose.

In a further embodiment, the coated particles are formed into a dosage form suitable for administration to a patient. In one embodiment, the coated particles are formed into a suspension, tablet, and/or capsule.

In several embodiments, the coating (e.g., enteric or non-enteric coating, such as acid-labile coatings) is adapted for administration through various routes selected from the group consisting of one or more of the following: oral, buccal, sublingual, nasal, topical, transdermal, ophthalmic, vaginal, rectal, intravesical, pulmonary, intra-arterial, intravenous, intradermal, intramuscular, subcutaneous, intraperitoneal, intrathecal and intraocular.

In one embodiment, the biologically active agent is selected from the group consisting of one or more of the following: testosterone, famotidine, halofantrine, and glyburide. One of skill in the art will understand that several agents can be used in accordance with embodiments of the invention. In one embodiment of the invention, the biologically active agent is a pharmaceutically active agent. In one embodiment, the biologically active agent is a poorly water soluble drug.

In yet another embodiment, the biologically active agent is a time-released agent. In some embodiments, the coating can be adapted, according to methods known in the art, to aid in the time-release function.

In some embodiments, one or more phospholipids are used. In one embodiment, the phospholipid is a phosphatidyl phospholipid. The phospholipid includes, but is not limited to, distearoyl phosphatidylcholine, dipalmitoyl phosphatidylcholine, dimyristoyl phosphatidylcholine, egg PC, soy PC, DMPG, DMPA, DPPG, DPPA, DSPG, DSPA, phosphatidylserine and sphigomyelin.

In one embodiment of the invention, the coating material is an enteric coating. In another embodiment, the coating is a non-enteric coating. In one embodiment, one coating is used. In another embodiment, more than one coating is used. In some embodiments, several different coatings are used, but they are all either enteric or non-enteric coatings. In some embodiments, a coated formulation is made by applying both enteric and non-enteric coatings. Thus, in one embodiment, advantages of both enteric coating and non-enteric (e.g., acid labile coatings) can be achieved because both types of coatings are applied to a powder comprising the biologically active agent. Layers of the same type of coating, or layers of different types of coatings, can be used to maximize certain desired results, e.g., time-release, increased absorption, decreased absorption, reduced gastrointestinal effects, increased bioavailability, etc.

In one embodiment, the enteric coating includes, but is not limited to, cellulose acetate phthalate, alginates, alkali-soluble acrylic resins, hydroxypropyl methylcellulose phthalate, methacrylate-methacrylic acid copolymers, polyvinyl acetate phthalate, styrol maleic acid copolymers, shellac, and cellulose acetate.

In another embodiment, the non-enteric coating includes, but is not limited to methylcellulose, ethylcellulose, hydroxyethylcellulose, methylhydroxyethylcellulose, hydroxypropylcellulose, hydroxypropylmethylcellolose, sodium carboxymethylcellulose, povidone, and polyethylene.

In one embodiment, the coating includes a plasticizer. One advantage of the plasticizer is that it increases the flexibility of the coating. Moreover, the plasticizer reduces the possibility of coating rupture and pore formation.

In yet another embodiment, the coating is a film plasticizer selected from the group consisting of phthalate esters, citrate esters and triacetin.

In another embodiment of the invention, a formulation is formed into a tablet, capsule, and/or suspensions. Suspensions include non-solids, gelatinous forms and liquids. In alternative embodiments, carriers, diluents and/or lubricants are also included in the formulation.

In one embodiment, removing the non-aqueous solvent comprises at least partially evaporating the solvent.

In one embodiment, the powder is coated with one or more acid-labile coatings. In some embodiments, coating comprises spraying the powder with a coating. In several embodiments, the powder is coated with one or more acid-labile coatings without having exposed said biologically active agent to an aqueous solvent. The term "powder" as used herein shall be given its ordinary meaning and shall also include fine particles, residue and concentrated materials.

In a further embodiment, at least one additional ingredient is combined with a biologically active agent. Additional ingredients can be active or inactive. Additional ingredients include, but are not limited to, carriers, diluents and lubricants. Additional ingredients also include, but are not limited to, microcrystalline cellulose, starch, lactose, talc, mannitol, polyethylene glycol, polyvinylpyrrolidone, hydroxypropylmethyl cellulose, ethyl cellulose, fatty acids, fatty acid salts, glyceryl behenate, dextrose and dicalcium phosphate.

In one embodiment, one or more surfactants are used. In one embodiment, a surfactant is added along with drug and phospholipid. Surfactants include, but are not limited to, polysorbates, bile salts, and alkyl glycosides. In one embodiment, a concentration of about 1% to about 50%, preferably about 5% to about 20%, surfactant is used.

In one embodiment of the invention, a method of making a composition for delivery of a chemical agent is provided. In one embodiment, the method comprises providing one or more phospholipids and providing one or more chemical agents. In one embodiment, the chemical agent is labile in an aqueous phase. The chemical agent and the phospholipids is then exposed to, or combined in, a non-aqueous solvent. The non-aqueous solvent is removed (for example, by evaporation), thereby making a powder. The powder is then coated or covered with one or more acid-labile coatings, thereby making coated particles. The more acid-labile coating contacts at least a portion of the powder. The chemical agent is not exposed to an aqueous phase prior to application of the coating. The coated particles are then synthesized or formed into a form suitable for delivery of said chemical agent. Chemical agents include chemical compounds such as nucleic acids, enzymes, food processing agents, etc.

A further embodiments of the invention relates to a compositions and formulations made according to the methods described above. In some embodiments, a proliposomal formulation comprising a lipophilic agent, a phospholipid and a coating is provided. In one embodiment, a method for delivering a pharmaceutical formulation to a mammal by administering the formulation to the mammal is provided. In some embodiments, the current invention relates to preventing, diagnosing or treating an illness in a mammal with the drug delivery system of the present invention.

DETAILED DESCRIPTION OF THE PREFERRED EMBODIMENT

Several embodiments of present invention relate to coated proliposomal formulations comprising a biologically active (e.g., pharmaceutically active) agent, a phospholipid and a coating material.

In some embodiments, an enteric coating is used. In other embodiments, an acid-labile coating is used. In one embodiment, the coated formulation enhances the dissolution and bioavailability of drugs. The effect is more pronounced for drugs with extremely low water solubility, such as halofantrine and testosterone. A less pronounced rate of dissolution is observed with drugs with higher water solubilities, such as famotidine. In one embodiment, the current invention consists of a drug delivery system which provides a more rapid onset of drug action, a longer duration of action and an increased $C_{max}$ as compared to administration of the drug alone. An enterically coated proliposomal formulation is provided in some embodiments (e.g., EnProLip™)

In a preferred embodiment, the formulation comprises
(a) a poorly water soluble drug;
(b) distearoyl phosphatidylcholine (DSPC), dipalmitoyl phosphatidylcholine (DPPC) or dimyristoyl phosphatidylcholine (DMPC); and
(c) cellulose acetate phthalate.

In one embodiment, the biologically active agent is a pharmaceutically active agents. In one embodiment, the pharmaceutically active agent is a poorly water soluble drug. Poorly water soluble drugs, as used herein, shall be given their ordinary meaning and shall include agents that require greater than approximately thirty (30) parts of solvent per one (1) part of solute to dissolve.

Examples of poorly water drugs include, but are not limited to, griseofulvin, famotidine, meclizine, cyclosporine, carbamazipine, methotrexate, itraconazole, dipyridamole, mercaptopurine, halofantrine, amiodarone, lomustine, testosterone, misoprostil, etoposide, rifamycin, azathioprine, glyburide, tolbutamide, aminoglutethimide, taxol, clofibrate, nifedipine, methyldopa, ramipril, dicumarol, and the like. One skilled in the art will appreciate that this invention is not limited to poorly water soluble drugs, but includes a wide range of pharmaceutically active and inactive agents. Drugs that are slightly soluble, sparingly soluble or hydrophilic may also be delivered using various embodiments of the present invention.

In a preferred embodiment, DSPC, DPPC or DMPC is used as the phospholipid. One skilled in the art will understand that other phospholipids, including, but not limited to, egg PC, soy PC, DMPG, DMPA, DPPG, DPPA, DSPG, DSPA, phosphatidylserine, sphigomyelin, and the like may be used.

In a preferred embodiment, cellulose acetate phthalate is used as the enteric coating. However, one skilled in the art will appreciate that alginates, alkali-soluble acrylic resins, hydroxypropyl methylcellulose phthalate, methacrylate-methacrylic acid copolymers, polyvinyl acetate phthalate, styrol maleic acid copolymers, shellac, cellulose acetate and the like may also be used. One skilled in the art will also appreciate that the enteric coating material used in various embodiments of the invention may include a combination of the aforementioned coatings.

In one embodiment of the invention, the coating material is a non-enteric coating. In one embodiment, non-enteric coatings include acid-labile materials. Non-enteric coatings, in some embodiments, include cellulose-based materials. Non-enteric coatings include, but are not limited to methylcellulose, ethylcellulose, hydroxyethylcellulose, methylhydroxyethylcellulose, hydroxypropylcellulose, hydroxypropylmethylcellolose, sodium carboxymethylcellulose, povidone, and polyethylene. One skilled in the art will also appreciate that the non-enteric coating material used in various embodiments of the invention may include a combination of the aforementioned enteric and non-enteric coatings.

In one embodiment, the coating includes a plasticizer. One advantage of the plasticizer is that it increases the flexibility of the coating. Moreover, the plasticizer reduces the possibility of coating rupture and pore formation. Plasticizers include, but are not limited to, phthalate esters, citrate esters and triacetin In one embodiment of the invention, the enteric coated proliposome delivery system will be used for anti-emetic purposes by preventing the release of noxious ingredients in the stomach, thereby reducing nausea and other adverse side effects.

In another embodiment of the invention, the enteric coated proliposomal formulation is used to deliver drugs which are susceptible to degradation in the intestinal tract.

In another embodiment, the invention will be used to administer drugs through various routes. Several embodiments will also be used to enhance delivery of drugs or other substances in the food industry, where enzyme immobilization is essential for various aspects of food processing. Thus, in some embodiments, methods of producing formulations for the delivery of one or more chemical agents is provided.

In a further embodiment, a method to treat a mammal comprising administering to the mammal a biologically active agent, a phospholipid and a coating material is provided.

One skilled in the art will understand that embodiments of the current invention are not limited to the delivery of drugs or biological/pharmaceutical agents. Any number of naturally occurring or synthetic substances, including diagnostic agents and therapeutic materials, may be delivered according to the current invention. These substances include, but are not limited to, anorexics, analgesics, antiarthritics, adrenergic blocking agents, steroids, vaccines, peptides, proteins, hormones, antibodies, antibiotics, antiviral agents, vitamins, nucleotides, nutritional agents, enzymes, genes, genetic material, cytotoxins, bacteria, microbes, viral agents, and the like. Placebo may also be administered using various embodiments of the current invention. Diluents, carriers, lubricants and the like, including, but not limited to, microcrystalline cellulose, starch, lactose, talc, mannitol, polyethylene glycol, polyvinylpyrrolidone, hydroxypropylmethyl cellulose, ethyl cellulose, fatty acids, fatty acid salts, glyceryl behenate, dextrose, dicalcium phosphate may also be administered using several embodiments of the present invention.

Further, one skilled in the art will understand that the amount of the active pharmaceutical or substance used in some embodiments of the current invention will depend on the dose required to be administered and/or the treatment desired. One skilled in the art will appreciate that "treatment" refers to any desired purpose for administering the pharmaceutically active ingredient, including prevention, control, cure, maintenance or improvement of health, and the like. By varying the concentration of the ingredients, size, number and/or amount of tablets, capsules, suspension or liquid, a wide range of doses may be orally administered. Similarly, varying the concentration of biologically active agents can vary the dose given through non-oral routes. The coatings may also be adapted for affecting the pharmacokinetics of the biological agent. Time-released drugs may also be administered according to various embodiments of the present invention. The coating may also affect the time release nature of the formulation.

One skilled in the art will also appreciate that the current invention is not limited to the delivery of a single pharmaceutical agent. Indeed, more than one pharmaceutical agent may be delivered simultaneously using the current drug delivery system. For example, in one "dose", the recipient may receive a combination of two or more drugs, at least one drug and a carrier, etc.

In one embodiment of the invention, the drug delivery system is synthesized in the following manner: At least one pharmaceutically active agent and at least one phospholipid are dissolved in solvent at appropriate ratios and concentrations. Upon dissolution, the solvent is evaporated to yield a dry powder-like material. The dried material is passed through a sieve-like apparatus. This dried material is then coated with a coating (enteric, non-enteric, or both), which is preferably in solution and can be sprayed onto the dried material. The coated particles are then used to synthesize tablet, capsule or liquid preparations suitable for delivery to a mammal. Alternatively, the coated particles are prepared in a form suitable for non-oral routes of administration (for example, in a patch for transdermal delivery or a spray for inhalation).

Several embodiments of the current invention are particularly advantageous because they allow for the enteric coating to be applied after the pharmaceutically active agent and phospholipid, are mixed. This permits preparation of different forms of the formulation, including, tablets, capsules, suspensions, or liquids. Moreover, various embodiment of the present invention allow for the facile preparation of tablets of various sizes. The size of the tablets, in one embodiment, is preferably controlled by adjusting the pore size of the mesh or sieve.

In one embodiment, one or more surfactants are used. In one embodiment, a surfactant is added along with drug and phospholipid. In other embodiments, a surfactant is added prior to making the powder, prior to coating the powder, or prior to forming the particles or granules into a dosage form. A surfactant, as used herein, shall be given its ordinary meaning and shall also include materials that reduce the surface tension of liquids. In some embodiments, the surfactant is an organic compound that contains both hydrophobic and hydrophilic groups, and are thus, in some embodiments, semi-soluble in both organic and aqueous solvents. In one embodiment, the surfactant is an amphipathic compound, such that it prefers to be in neither phase (water or organic). For this reason, in some embodiments, the surfactant locates at the phase boundary between the organic and water phase. Surfactants, in some embodiments, can also congregate together and form micelles.

Surfactants include, but are not limited to, polysorbates, bile salts, and alkyl glycosides. Surfactants also include soaps, sulfonates, sulfates, fatty acid isethionates, fatty acid sarcosinates, fatty acid taurides, N-acylamino acids, fatty alcohol polyglycol ethers, alkylphenol polyglycol ethers, fatty acid polyglycol esters, fatty acid amide polyglycol ethers, fatty amine polyglycol ethers, alkoxylated triglycerides, protein hydrolyzates, polyol fatty acid esters, sugar esters, sorbitan esters, amine oxides, quatenary ammonium compounds, alkylbetaines, alkylamidobetaines, amino-propionates, aminoglycinates, imidazolinium betaines and sulfobetaines. In some embodiments, a concentration of about 1% to about 50%, preferably about 5% to about 20%, surfactant is used.

Some embodiments of the present invention that use one or more surfactants have certain advantages. For example, surfactants can (1) form mixed micelles, and upon dilution can produce liposomes; (2) maintain the integrity of protein molecules in the formulation; (3) improve encapsulation of hydrophilic molecules; and (4) help liposomes to become more deformable, thereby, allowing them to deliver drugs through absorption barriers.

I previously described a method for preparing drugs in a tablet or capsule form with an enteric coating. However, a particular advantage of various embodiments of the current invention is the ability to generate suspension or liquid forms of the formulation. Suspension or liquid forms are sometimes preferable because they do not affect gastrointestinal motility to the same extent as do capsules or tablets. For most drugs, it is important that that the pharmaceutically active compound is not eliminated in the gastrointestinal tract before it has had a chance to exert a localized effect or to pass into the bloodstream. When a formulation is in a suspension or liquid form, it is typically retained in the intestine for longer periods of time and, as such, absorption is increased as compared to capsules or tablets. Various aspects of this invention also provide for flexibility in the surface area of the formulation. Whereas tablets are generally restricted to a fixed surface area, several embodiments of the present invention permit the use of capsules, suspensions and liquids, which may provide a larger surface area and hence contribute to increased absorption and bioavailability.

I previously described a method for delivering drugs in which the drug was exposed to an aqueous phase. According to several embodiments of the current invention, the lipid and the drug are exposed to chloroform, or similar solvent. There is no exposure to an aqueous phase. For water sensitive drugs and drugs that are labile in water, such as antibodies, the absence of an initial aqueous phase preserves the integrity of these drugs. Further, because there is no exposure to an aqueous phase, liposomes are not formed. Hence, several embodiments of the current invention are directed to non-liposomal pharmaceutical formulations. As used herein, "non-liposomal" is defined as a formulation which is not exposed to an aqueous phase, and thus does not form liposomes, prior to the application of the enteric coating.

Not wishing to be bound by the following description, it is believed that one embodiment of the current invention works as follows: After formation of the proliposome formulation, the formulation is orally delivered to a mammal. When the proliposome formulation encounters an aqueous phase at a pH at or above approximately 7.0, liposomes are formed and the drug molecules are transported across the gastrointestinal membrane.

Specific Routes of Administration

According to one aspect of this invention, the formulation is administered through various routes including, but not limited to, oral, buccal, sublingual, nasal, topical, transdermal, ophthalmic, vaginal, rectal, intravesical, pulmonary, intra-arterial, intravenous, intradermal, intramuscular, subcutaneous, intraperitoneal, intrathecal and intraocular.

With respect to the transdermal route, several embodiments of this invention are particularly advantageous because iontophoretic transdermal delivery of drugs is hindered if the drug molecules are not charged at pH suitable for this kind of delivery. However, an enteric-coated proliposomal formulation in accordance with various embodiments of the current invention may be successfully used for transdermal delivery. The enteric coating protects the drug from acidic pH. Non-enteric coatings can also be used. The charge on the liposomes facilitates drug delivery by iontophoretic transdermal delivery. Certain embodiments of this invention are especially useful for water-insoluble drugs or poorly soluble drugs. Typically, in order deliver drugs iontophoretically, the drug must first be dissolved. Therefore, water-insoluble drugs or poorly soluble drugs are difficult to administer by this method. In accordance with several embodiments of the present invention, however, the water-insoluble drugs or poorly soluble drugs can be incorporated in liposomes for delivery by this route. To facilitate preparation of drugs for transdermal delivery, the formulation may be suspended in an aqueous phase to facilitate absorption from the skin. In one embodiment, the pH of the solution is preferably neutral to facilitate dissolution of the coating.

In one embodiment of the current invention, a method for nasal administration is provided. If local action of a drug is desired instead of a systemic effect, the proliposomal formulations of several embodiments described herein are ideal because they are non-irritating to the mucosal membranes. The formulation is believed to non-irritating because the mucosa is primarily in contact with the lipid bilayers, rather than directly with the irritating drug. The release of drug from liposome is in a sustained fashion and readily miscible with secretions covering these membranes.

In another embodiment of the current invention, a method for pulmonary administration is provided. Proliposomes have been to shown to be a very useful and efficient system for pulmonary drug delivery. The proliposomal formulations can be administered using dry powder inhalers. Administration of proliposomal formulations by pulmonary route can modify pulmonary absorption, resulting in localized drug action in the respiratory tract, a prolonged drug presence in the circulation and decreased systemic side effects. Hence, from a toxicological viewpoint, proliposomes would seem a particularly appropriate system for drug delivery to the lungs.

Both enteric and/or non-enteric coating can be used in accordance with the routes of administration described herein. If administration of the pharmaceutical formulations described herein are to be delivered to a target in which the environment is acidic, the enteric coating may not dissolve, thus hampering drug release. In some cases, this may be desired. However, in several embodiments, a non-enteric coating is provided. Non-enteric coatings, in some embodiments, include polymers that dissolve at acidic, basic and neutral pH. Based upon the desired target tissue for drug delivery, one skilled in the art will understand which type of coating should be used in accordance with embodiments of the present invention.

The following Examples illustrate various embodiments of the present invention and are not intended in any way to limit the invention.

Example 1

Halofantrine and distearoyl phosphatidylcholine (1:3 ratio) were dissolved in chloroform and the solvent was evaporated using nitrogen gas. The dry powder was passed through a #60 mesh screen. Cellulose acetate phthalate (50 mg) was dissolved in acetone (6 ml) and sprayed on the halofantrine and distearoyl phosphatidylcholine mixture.

Dissolution was carried out using 40 mg of the formulation using a Type II USP dissolution apparatus. The dissolution medium (250 ml) was phosphate buffered saline (pH 7.4). The temperature of the dissolution media was maintained at 37±0.5° C. and the rotation of the paddle was set at 50 rpm. Samples (5 ml) were withdrawn at 5, 10, 15, 30, 45, 60, 90, 120, 180 and 240 minutes. Equal volumes of phosphate buffered saline were added to maintain a constant volume of dissolution media.

The samples were analyzed by high performance liquid chromatography (HPLC). In the mobile phase, 46.5:53.5 (0.025 M potassium phosphate/sulfuric acid/triethylamine solution): acetonitrile was combined, mixed and filtered using a Kontes filter apparatus. Sodium dodecyl sulfate (1.1 g/L of mobile phase) was added to the filtered solution.

The parameters of the assay procedure was as follows. The flow rate was set at 1.2 ml/minute. The temperature was ambient. The run time was 30 minutes. The ultraviolet light detector was set at a wavelength of 254 nm. The retention times for (+) halofantrine and (−) halofantrine were 25 minutes and 28 minutes respectively.

The pharmacokinetic parameters of the enteric coated proliposomal formulation of halofantrine were evaluated as follows. The proliposomal product was prepared as a suspension in 0.78% methylcellulose. A non-liposomal suspension formulation (control) was prepared by dispersing halofantrine powder in 1% methylcellulose. Sprague-Dawley rats were cannulated at the right jugular vein under halothane anesthesia. After an overnight rest, the rats were given 7 mg/kg of a halofantrine suspension as either the proliposomal (7 rats) or control (6 rats) formulation by oral gavage. Serial blood samples were obtained from the cannula until 48 h post-dose. A stereospecific HPLC assay was used to measure plasma concentration of halofantrine enantiomers. Noncompartmental pharmacokinetic methods were used to determine $AUC_{0-24}$, $C_{max}$ and $t_{max}$. Student's unpaired t-test was used to assess significance of differences. Results (mean±SD) are provided in Table 1.

TABLE 1

Pharmacokinetic Results of the Halofantrine Study

| | AUC, µg × h/mL | | Cmax, ng/mL | | Tmax, h | |
|---|---|---|---|---|---|---|
| | Control | Liposome | Control | Liposome | Control | Liposome |
| (+)-HF | $5.2 \pm 0.81^b$ | $7.7 \pm 1.8^{a,b}$ | $391 \pm 59.2^b$ | $722 \pm 170^{a,b}$ | $7.0 \pm 2.8$ | $4.1 \pm 2.3$ |
| (−)-HF | $1.9 \pm 0.53$ | $2.6 \pm 0.66^a$ | $196 \pm 42.3$ | $360 \pm 80.5^a$ | $4.6 \pm 2.1$ | $4.0 \pm 1.3$ |

$^a$ = p < 0.05 compared to control;
$^b$ = p < 0.05 compared to antipode.

One skilled in the art will have sufficient information to make and use the non-liposomal formulations of the present invention by adapting the description provided below for cellulose acetate phthalate.

The proliposomal formulation displayed higher bioavailability of both enantiomers than did the control formulation. The AUC and $C_{max}$ of halofantrine enantiomers increased by over 40% and 80%, respectively. Although the mean tmax was lower for both enantiomers in the proliposomal formulation, the differences from control were not statistically significant.

Example 2

Testosterone and phospholipid (DMPC, DPPC or DSPC; 1:1 ratio) were dissolved in chloroform. Chloroform was evaporated using nitrogen gas. The dry powder was passed using a #60 mesh sieve. Cellulose acetate phthalate (40 mg) was dissolved in acetone (5 ml) and the resulting solution was sprayed on the solid dispersion containing the testosterone and phospholipid. Nitrogen gas was used to dry the powder.

Dissolution was carried out using 45 mg of the formulation using a Type II USP dissolution apparatus. The dissolution medium (300 ml) was phosphate buffered saline (pH 7.4). The temperature of the dissolution media was maintained at 37±0.5° C. and rotation of the paddle was set at 50 rpm. The samples (5 ml) were withdrawn at 2, 5, 8, 10, 15, 20, 25, 30, 40, 50, 60, 80, 100, and 120 minutes. Equal volumes of phosphate buffered saline were added to maintain a constant volume of dissolution media. Dissolution samples were analyzed by measuring the absorbance at 254 nm.

Figure 1:
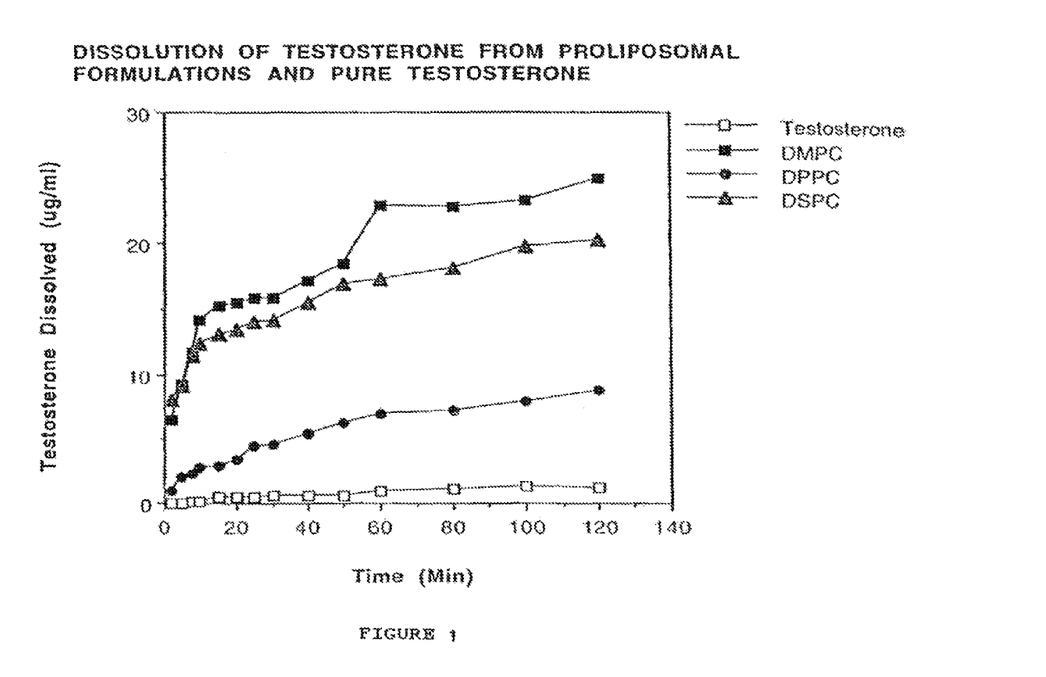
FIG. 1 shows a comparison among dissolution rates of testosterone using various proliposomal formulations and pure testosterone.
Figure 2:
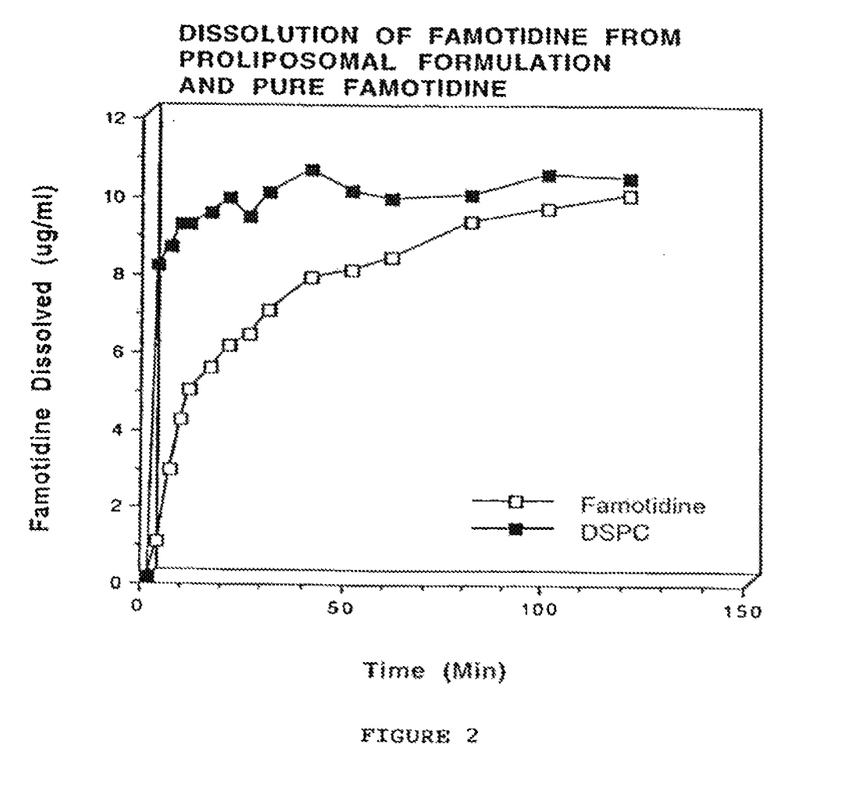
FIG. 2 shows a comparison between dissolution rates of famotidine using a proliposomal formulation (DSPC) and pure famotidine.

The rate and extent of dissolution of testosterone was significantly greater with all proliposomal formulations as compared to pure testosterone as shown in FIG. 2. The extent of dissolution was highest with the proliposomal formulation containing DMPC, followed by DSPC and DPPC. This may be explained by the phase transition temperature (Tc) of these lipids. DPPC has a Tc of 41° C., which is very close to the temperature of the dissolution study (37° C.). DMPC and DSPC have Tc's of 23° C. and 56° C. respectively. DMPC exists in a fluid state and DSPC in a gel state at 37° C. Because the Tc of DPPC was similar to the temperature of the dissolution study, the formulation may have been unstable, thus hampering the dissolution of testosterone. Nonetheless, the data indicates that the rate and extent of dissolution of testosterone was increased by using the enteric coated proliposomal formulation.

Example 3

Famotidine and distearoyl phosphatidylcholine (DSPC; 1:3 ratio) were dissolved in chloroform. Chloroform was evaporated using nitrogen gas. The dry powder was passed using a #60 mesh sieve. Cellulose acetate phthalate (50 mg) was dissolved in acetone (5 ml) and the resulting solution was sprayed on the solid dispersion containing testosterone and phospholipid. Nitrogen gas was used to dry the powder.

Dissolution was carried out using 87 mg of the formulation using a Type II USP dissolution apparatus. The dissolution medium (300 ml) was phosphate buffered saline (pH 7.4). The temperature of the dissolution media was maintained at 37±0.5° C. and the paddle rotation was set at 50 rpm. The samples (5 ml) were withdrawn at 2, 5, 8, 10, 15, 20, 25, 30, 40, 50, 60, 80, 100, and 120 minutes. Equal volumes of phosphate buffered saline were added to maintain a constant volume of dissolution media. Dissolution samples were analyzed by measuring the absorbance at 285 nm.

The rate of dissolution of famotidine formulation was significantly greater than pure famotidine. However, there was no significant increase in the extent of dissolution of famotidine in PBS. Because the proliposomal formulation results in a faster rate of dissolution, in some embodiments, the onset of drug action will be more rapid.

Example 3

One embodiment of the present invention was compared to a control method for producing pharmaceutical formulations. The control method used in the following examples is disclosed by Ganter in U.S. Pat. No. 5,635,206, herein incorporated by reference, at Example 1, except that the percentage of water used was 5% and 0%. To exemplar drugs which are poorly water soluble were used: glyburide and benzocaine.

The following tables summarize the protocol used and the results.

TABLE 2

Protocol Materials Used In Comparison Studies of Glyburide

| Material | Quantity Used In Control Method Using 5% Water | Quantity Used In Control Method Using 0% Water | Quantity Used In Applicant's Method |
|---|---|---|---|
| Glyburide | 12% | 12% | 12% |
| Lecithin (DMPC) | 63% | 63% | 63% |
| Water | 5% | 0% | 0% |
| Ethanol | 20% | 25% | 25% |

TABLE 3

Protocol Materials Used In Comparison Studies of Benzocaine.

| Material | Quantity Used In Control Method Using 5% Water | Quantity Used In Control Method Using 0% Water | Quantity Used In Applicant's Method |
|---|---|---|---|
| Benzocaine | 12% | 12% | 12% |
| Lecithin (DMPC) | 63% | 63% | 63% |
| Water | 5% | 0% | 0% |
| Ethanol | 20% | 25% | 25% |

TABLE 4

Results For Comparison Studies of Glyburide

| Glyburide | Control Method With 5% Water | Control Method With 0% Water | Applicant's Method |
|---|---|---|---|
| Texture | Milky | Milky | Powder |
| Yield (%) | 69.40% | 55.30% | 97.80% |
| Absorbance | 3.8177 | 3.9141 | 1.9446 |
| Particle Size | 2.544 μm | 5.978 μm | 8.638 μm |

TABLE 5

Results For Comparison Studies of Benzocaine

| Benzocaine | Control Method With 5% Water | Control Method With 0% Water | Applicant's Method |
|---|---|---|---|
| Texture | Clear Solution | Clear Solution | Powder |
| Yield (%) | 68.09% | 68.20% | 97.80% |
| Absorbance | 3.6030 | 3.6130 | 3.7377 |
| Particle Size | 1.190 μm | 3.830 μm | 9.163 μm |

The results for glyburide and benzocaine showed that some embodiments of the current invention have unexpected and marked advantages over control methods at 5% water and at 0% water. For example, some embodiments of the present invent can result in: (1) significantly higher yield; (2) more effective and efficient incorporation with the lipid, which was shown by a lower absorbance value in the aqueous phase; (3) larger particle size, which is advantageous for ease of coating and increased stability and absorption in the gastrointestinal tract; and/or (4) powder-like texture, which is easier to manipulate and coat than a milky texture. Some embodiments of the present invention have one or more of the aforementioned advantages. Because, in one embodiment, the current method does not expose the drug to an aqueous phase and evaporates the non-aqueous solvent to produce a product that is capable of being coated, the quality and quantity of the formulation is markedly improved.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A dosage form comprising:
    a proliposomal powder comprised of a dispersion of testosterone and phospholipid, and
    an enteric coating.
2. A dosage form of claim 1, further comprising a capsule and wherein the proliposomal powder is contained within the capsule.
3. A dosage form of claim 2, wherein the capsule is coated with an enteric coating.
4. A dosage form of claim 1, wherein the phospholipid is selected from the group consisting of one or more of the following: distearoyl phosphatidylcholine, dipalmitoyl phosphatidylcholine, dimyristoyl phosphatidylcholine, egg PC, soy PC, DMPG, DMPA, DPPG, DPPA, DSPG, DSPA, phosphatidylserine and sphigomyelin.
5. A dosage form of claim 4, further comprising a surfactant.
6. A dosage form of claim 4, wherein the enteric coating is at least one of, cellulose acetate phthalate, alginates, alkali-soluble acrylic resins, hydroxypropyl methylcellulose phthalate, methacrylate-methacrylic acid copolymers, polyvinyl acetate phthalate, styrol maleic acid copolymers, shellac, and cellulose acetate.
7. A dosage form of claim 4 wherein the phospholipid is distearoyl phosphatidylcholine.
8. A dosage form of claim 4 further comprising an additional ingredient selected from a carrier, a diluent, a lubricant and mixtures thereof.
9. A dosage form of claim 8, further comprising a plasticizer selected from the group consisting of phthalate esters, citrate esters and triacetin.
10. A dosage form of claim 8, wherein the additional ingredient is selected from at least one of microcrystalline cellulose, starch, lactose, talc, mannitol, polyethylene glycol, polyvinylpyrrolidone, hydroxypropylmethyl cellulose, ethyl cellulose, fatty acids, fatty acid salts, glyceryl behenate, dextrose, dicalcium phosphate.
11. A dosage form of claim 1, wherein the dosage form is a tablet or capsule.
12. A proliposomal powder comprised of a dispersion of testosterone and phospholipid.
13. A proliposomal powder of claim 12, wherein the phospholipid is selected from the group consisting of one or more of the following: distearoyl phosphatidylcholine, dipalmitoyl phosphatidylcholine, dimyristoyl phosphatidylcholine, egg PC, soy PC, DMPG, DMPA, DPPG, DPPA, DSPG, DSPA, phosphatidylserine and sphigomyelin.
14. A proliposomal powder of claim 13, further comprising a surfactant.
15. A proliposomal powder of claim 12 coated with an enteric coating selected from cellulose acetate phthalate, alginates, alkali-soluble acrylic resins, hydroxypropyl methylcellulose phthalate, methacrylate-methacrylic acid copolymers, polyvinyl acetate phthalate, styrol maleic acid copolymers, shellac, cellulose acetate, and mixtures thereof.
16. A proliposomal powder of claim 13, wherein the phospholipid is distearoyl phosphatidylcholine.
17. A method of treating a patient in need of testosterone comprising the step of:
    administering a dosage form of claim 1.
18. A method of treating a patient in need of testosterone comprising the step of:
    administering a dosage form of claim 4.
19. A method of making a proliposomal dispersion of testosterone and a phospholipid, comprising the steps of:
    dissolving testosterone and at least one phospholipid in a non-aqueous solvent without exposure to an aqueous phase to form a solution, and
    removing the non-aqueous solvent to form a dry powder dispersion comprising the testosterone and at least one phospholipid.
20. A method of claim 19, wherein the phospholipid is selected from the group consisting of one or more of the following: distearoyl phosphatidylcholine, dipalmitoyl phosphatidylcholine, dimyristoyl phosphatidylcholine, egg PC, soy PC, DMPG, DMPA, DPPG, DPPA, DSPG, DSPA, phosphatidylserine and sphigomyelin.

* * * * *